US005976519A

United States Patent [19]

Nojiri et al.

[11] Patent Number: 5,976,519

[45] Date of Patent: Nov. 2, 1999

[54] YOLK ANTIBODY-CONTAINING HAIR CARE PRODUCT

[75] Inventors: Hiroshi Nojiri, Utsunomiya; Sachio Naito, Tochigi-ken; Hidehisa Takahashi, Yokkaichi; Masaru Fujiki, Yokkaichi; Mujo Kim, Yokkaichi, all of Japan

[73] Assignees: Kao Corporation, Tokyo; Taiyo Kagaku Co., Ltd., Yokkaichi, both of Japan

[21] Appl. No.: 07/974,510

[22] Filed: Nov. 12, 1992

[30] Foreign Application Priority Data

Nov. 14, 1991 [JP] Japan .................................. 3-325057

[51] Int. Cl.[6] ................................................ A61K 7/06

[52] U.S. Cl. .................... 424/70.14; 424/581; 424/70.1; 514/880

[58] Field of Search ................................ 424/70, 581, 88

[56] References Cited

U.S. PATENT DOCUMENTS

| | | | |
|---|---|---|---|
| 1,690,752 | 11/1928 | Postenak | 424/581 |
| 3,987,161 | 10/1976 | Widder . | |
| 4,228,054 | 10/1980 | Ona et al. . | |
| 4,240,450 | 12/1980 | Grollier et al. . | |
| 4,396,388 | 8/1983 | Hojo et al. . | |
| 4,445,521 | 5/1984 | Grollier et al. . | |
| 4,597,962 | 7/1986 | Grollier et al. . | |
| 4,719,099 | 1/1988 | Grollier et al. . | |
| 5,009,880 | 4/1991 | Grollier et al. . | |

FOREIGN PATENT DOCUMENTS

| | | | |
|---|---|---|---|
| 1936432 | 12/1970 | Germany | 424/581 |
| 3018456 | 11/1981 | Germany | 424/581 |
| 57-23 631 | 2/1982 | Japan . | |
| 57-163 392 | 10/1982 | Japan . | |
| 61-280 413 | 12/1986 | Japan . | |
| 64-9913 | 1/1989 | Japan . | |
| 64-38 098 | 2/1989 | Japan . | |

OTHER PUBLICATIONS

Tizard, Ian R. *An Introduction to Veterinary Immunology*, (1977) p. 168.

Patent Abstracts of Japan, vol. 16, No. 213, (C–942), JP–A–40 41 413, Feb 12, 1992, Hideyo Uchiwa, et al., "Hair Modifying Agent".

*Primary Examiner*—Thurman K. Page
*Assistant Examiner*—Brian K. Seidleck
*Attorney, Agent, or Firm*—Oblon, Spivak, McClelland, Maier & Neustadt, P.C.

[57] ABSTRACT

A hair care product contains a yolk antibody (a yolk-derived, anti-hair antibody) which has been obtained from an egg of a domestic fowl immunized using, as an antigen, whole human hair, e.g., normal human hair or human hair damaged by permanent waving, dyeing or bleaching, hair particles obtained by grinding constituent tissues of human hair, the keratin protein extracted from the human hair, or a hydrolysate of the keratin protein.

17 Claims, No Drawings

YOLK ANTIBODY-CONTAINING HAIR CARE PRODUCT

BACKGROUND OF THE INVENTION

1) Field of the Invention

This invention relates to a hair care product containing a yolk antibody, and more specifically to a hair care product which contains as an effective ingredient a yolk antibody obtained from an egg of a domestic fowl immunized using human hair (which may hereinafter be called simply "hair" for the sake of brevity) as an antigen, can impart good touch feeling to hair, and can reduce hair damage.

2) Description of the Related Art

Keeping step with the increase in individual choice of fashion in recent years, the tendency of preference toward long hair has steadily taken root. In addition, there is also increased diversity as to the style of long hair available because of hairdressing such as localized or partial head permanent waving. Reflecting this, hair damage such as split and broken hair is also increasing steadily.

Such hair damage is considered to have occurred because the structure of hair was weakened due to modification of the keratin protein by chemical treatment such as permanent waving, making the hair more susceptible to physical influences such as hot-air blowing and brushing.

As a measure for the prevention of such hair damage, it is known to add collagen, keratin protein, egg albumin protein or the like to various hair care products in order to cope with deterioration of the protein structure due to chemical treatment, thereby to form a protective film on the surface of hair and to improve the water retaining property and flexibility (Japanese Patent Application Laid-Open No. 280413/1986).

Although protein components such as collagen, keratin protein and egg albumin protein can exhibit some benefit in the prevention of damage by chemical treatment of hair, these effects are not fully satisfactory.

To improve set retention, it is also known that an antiserum which has been obtained using hair particles as an antigen (U.S. Pat. No. 3,987,161 which is hereby incorporated herein by reference) will improve the hair.

However, the antiserum used in the above method is obtained from the blood of an animal immunized with hair particles. The procedure for obtaining the antiserum is therefore irksome and, moreover, the yield available from a single practice of the procedure is low, so that the above method is not considered satisfactory industrially.

In particular, it is well known that an antiserum obtained from a mammal has complement-activating effects so that it tends to stimulate neutrophils to cause local inflammation. It is therefore preferred not to use a mammal antiserum in hair care products. Further, an antiserum is an antibody obtained from the blood of an animal so that the antiserum is undesirable from the standpoint of animal protection.

With a view toward reducing the frictional force on the surface of hair, on the other hand, an oil component such as a higher alcohol, an ester oil, fluid paraffin or silicone oil is added to and utilized in hair rinse agents, hair treatment agents, hair brushing agents and the like.

It is, however, the current situation that such oil components cannot achieve satisfactory treatment effects for damaged hair although they show certain effects for the prevention of hair damage. Further, use of an oil component in a large proportion in hair care products results in an increase in stickiness and greasiness and may hence impair how the hair feels after use.

SUMMARY OF THE INVENTION

It has therefore been desired to develop a hair care product which is free from stickiness or greasiness, is excellent in conditioning effects such as how the hair feels after use, has long-lasting properties, can prevent hair damage and, moreover, can specifically act on damaged parts of hair and effectively restore the hair to its inherent potential.

To overcome the above-described problems, the present inventors have conducted extensive research. As a result, it has been found that use of a hair care product, to which has been added a yolk antibody prepared from an egg of a domestic fowl immunized using human hair as an antigen, for hair subjected to chemical treatment such as permanent waving can impart a surprising range of conditioning effects such as moisturized feeling, flexibility, smoothness, prevention and restoration of split hair, and luster even in a dry state and these effects are not lost even after several shampooings, leading to the completion of the present invention.

The present invention therefore provides a hair care product comprising a yolk antibody which has been obtained from an egg of a domestic fowl immunized using human hair as an antigen.

The hair care product according to the present invention, which contains the yolk-derived anti-hair antibody, can impart excellent conditioning effects such as moisturizing, flexibility, smoothness, prevention and restoration of split hair and luster to hair even in a dry state, so that a feeling of being good to touch can be imparted to the hair. Its effects are not lost even after several shampooings.

The antibody used in the present invention is a yolk antibody so that it can be prepared easily in a large quantity. Moreover, the antibody has the additional advantage that it does not have complement-activating effects and is hence free of the potential danger of local inflammation.

In addition, a yolk antibody obtained using as an antigen hair damaged by permanent waving or the like specifically acts on damaged parts of hair.

The hair care product according to this invention can, therefore, be used widely as having excellent effects for the prevention of hair damage such as split and broken hair and for the conditioning of hair.

DETAILED DESCRIPTION OF THE INVENTION AND PREFERRED EMBODIMENTS

The yolk antibody, which is added to the hair care product according to the present invention and is prepared from an egg of a domestic fowl immunized using hair as an antigen (which hereinafter may also be abbreviated as a "yolk-derived, anti-hair antibody"), can be obtained from a water-soluble fraction prepared by immunizing a domestic fowl with hair constituent particles, diluting the yolk of an egg, which has been laid by the domestic fowl, with an aqueous solution of a polysaccharide (preferably an aqueous solution of a polysaccharide having a high molecular weight, for example, an aqueous solution of carrageenan), and then centrifuging the thus-diluted mixture to remove coagulates of lipoproteins. This water-soluble fraction can be used as is or after either purifying or concentrating it by a method commonly employed for the purification of proteins such as salting out or ion-exchange chromatography.

Usable examples of the domestic fowl to be immunized include hens, ducks, quail and the like. From the standpoint of mass productivity of the antibody, it is desirable to use an egg-breed domestic fowl such as White Leghorn.

Illustrative usable examples of the hair as the antigen include whole hair such as normal hair or hair damaged by permanent waving, dyeing, bleaching or the like as well as hair particles obtained by grinding hair constituent tissues such as hair cuticles or hair cortices to lengths not greater than 100 $\mu$m, the keratin protein extracted from the hair, and a hydrolysate of the keratin protein. To obtain an antibody specific to damaged hair, it is also possible to use, as an antigen, the above hair particles or keratin protein after applying chemical treatment such as permanent waving to the same.

To grind hair for use as an antigen, several methods are known including that in which hair is swollen with water and then freeze-ground as proposed in a preceding application (now Japanese Patent Application Laid-Open No. 163392/1982) and the method in which hair is treated with a protein modifier such as lithium bromide, urea or guanidine hydrochloride, swollen, frozen and then ground in the presence of liquefied nitrogen by a known grinder such as a mortar or sand mill. The grinding is however not limited to such methods but can be conducted by any other appropriate method. Illustrative constituent tissues of hair include hair cuticles, hair cortices and hair medullas. Particulate hair cuticles can be obtained by a known method, for example, by shaking hair, which has been chopped to lengths not greater than 1 cm, together with TEFLON® balls in sterilized water to mechanically separate particulate hair cuticles. On the other hand, particulate hair cortices can be obtained by processing, in accordance with the above-described grinding method for hair, hair from which hair cuticles have been removed by the Vantiane treatment disclosed in U.S. Pat. No. 4,396,388 which is hereby incorporated herein by reference.

Further, keratin protein from hair can be obtained by using a known method, for example, by extracting it with a protein modifier such as urea, guanidine chloride or sodium dodecylsulfate in the presence of a reducing agent such as mercaptoethanol, dithiothreitol, tributylphosphine or thioglucolic acid. Although the hair keratin protein can be used as an antigen without any further treatment, it can be used after treating it with iodoacetic acid, iodoacetamide, N-ethylmaleimide or the like to block thiol groups or after fractionating it by chromatography. The hydrolysate of hair keratin can be obtained by the known method disclosed in Japanese Patent Application Laid-Open No. 23631/1982.

To immunize a domestic fowl by using the above-described hair, conventional methods can be adopted, including subcutaneous injection, intraperitoneal injection, intramuscular injection or the like of hair particles, hair keratin and/or the hair keratin hydrolysate to the domestic fowl; and addition of hair particles, hair keratin and/or the hair keratin hydrolysate to feed or water, followed by their oral administration together with the feed or water to the domestic fowl to immunize the same. At this time, an adjuvant can also be used in combination as needed.

To obtain a yolk antibody from an egg immunized as described above, a known method or its analogous method can be used. For example, an industrial purification method of a yolk antibody is disclosed in detail in Japanese Patent Application Laid-Open No. 38098/1989. The present invention is however not limited to the above exemplary purification method but can be practiced by using any other appropriate known method.

As one example of the yolk-derived anti-hair antibody usable in the present invention, a partial purification product of a supernatant obtained by adding an aqueous solution of λ-carrageenan to an egg yolk can be mentioned. Further, a purified, yolk-derived anti-hair antibody having a still higher antibody titer potency can be obtained, for example, by extracting and isolating an immunoglobulin contained in an egg yolk.

The yolk-derived anti-hair antibody can be added in the form of a solution to provide the hair care product according to the present invention. It is however preferred to use it after concentration or drying. Preferably, the concentration can be conducted by conventional distillation under reduced pressure and the drying can be performed by lyophilization.

To obtain the hair care product according to the present invention, yolk-derived anti-hair antibodies obtained as described above are added either singly or in combination. The proportion of the yolk-derived anti-hair antibody in the hair care product may be, for example, 0.01–50 wt. % or so (hereinafter indicated merely by "%"), preferably 0.01–20% when calculated as a partially-purified lyophilization product; or 0.001–5% or so, preferably 0.005–1% when calculated as a fully-purified lyophilization product. If the proportion in terms of the purified, yolk-derived anti-hair antibody is smaller than 0.001%, the yolk-derived anti-hair antibody cannot exhibit its effects fully. Any proportions greater than 5%, however, are not expected to improve its effects in proportion to the increments.

No particular limitation is imposed on hair care products to which the yolk-derived anti-hair antibody can be added in accordance with the present invention. The yolk-derived anti-hair antibody can be added to any hair care products including, for example, preshampoos, shampoos, hair rinses, hair conditioners, hair treatment agents, setting lotions, blow styling lotions, hair sprays, foamed styling agents, jelly styling agents, hair liquids, hair tonics, hair creams, first-package permanent wave formulations, second-package permanent wave formulations, permanent hair dyes, and temporary hair dyes.

The preparation form of the hair care product according to this invention can be suitably chosen in accordance with its application purpose from various preparation forms such as an aqueous solution, an ethanol solution, an emulsion solution, an emulsion, a suspension, a gel, a liquid crystal, a solid and an aerosol.

In addition to the above-described yolk-derived anti-hair antibody as the essential ingredient, various known ingredients for hair care products can be added to the hair care product of this invention. These known ingredients include, for example, anionic surfactants such as alkyl benzene sulfonates, alkyl ether sulfonates, olefin sulfonates, α-sulfofatty acid esters, amino acid surfactants, phosphate ester surfactants, and sulfosuccinate ester surfactants; amphoteric surfactants such as sulfonic acid type surfactants, betaine type surfactants, alkyl amine oxides, and imidazoline type surfactants; nonionic surfactants such as polyoxyethylene alkyl ethers, polyoxyethylene alkylphenyl ethers, alkanol amides and alkylene oxide adducts thereof, sorbitan fatty acid esters of polyhydric alcohols and fatty acids, and alkylsaccharide surfactants; and cationic surfactants such as mono- or di-long-and-straight-chain alkyl quaternary ammonium salts and mono- or di-long-and-branched-chain alkyl quaternary ammonium salts. These surfactants can be used either singly or in combination in accordance with the properties of each hair care agent.

Where the hair care agent according to the present invention is a shampoo, in particular, it is preferred in view of irritation to the skin or hair to use an amino acid surfactant, a phosphate ester surfactant, a sulfosuccinate ester surfactant, an imidazoline type surfactant, an alkyl saccharide surfactant or the like among the surfactants described above.

When such a surfactant is added to the hair care product of this invention, its preferred proportion can be 0.01–40.0% or so, especially 0.5–20.0% or so.

To improve the touch feeling to hair or skin, the hair care product according to this invention can contain one or more cationic polymers such as cationized cellulose derivatives, cationic starch, cationized guar gum derivatives, diallyl quaternary ammonium salts/acrylamide non-mixtures, quaternized polyvinyl-pyrrolidone derivatives and polyglycol-polyamine condensation products.

Preferred specific examples of these cationic polymers include cationized celluloses having a molecular weight of about 100,000–3,000,000; cationized starches having a cationization degree of about 0.01–1; cationized guar gums having a cationization degree of about 0.01–1 ("JAGUAR", trade mark; product of Mayhall Company); diallyl quaternary ammonium salt/acrylamide copolymers having a molecular weight of about 30,000–2,000,000; quaternized polyvinyl pyrrolidone derivatives having a molecular weight of about 10,000–2,000,000 and a cationic nitrogen content of 1.8–2.4% in the vinyl polymers, such as quaternized polyvinyl-pyrrolidone-dimethylaminoethyl methacrylate copolymers; $C_{6-20}$ alkyl-containing polyglycol-polyamine condensation products; adipic acid-dimethylaminohydroxypropyl diethylenetriamine copolymers ("Cartaletin", trade mark; product of Sandoz Corporation); and cationic polymers disclosed in U.S. Pat. Nos. 4,240,450, 4,445,521, 4,719,099, 5,009,880 and 4,597,962, all of which are hereby incorporated herein by reference.

When these cationic polymers are added to the hair care product of this invention, its preferred proportion can be 0.05–20.0% or so, especially 0.1–10.0% or so.

To improve the tough feeling to hair or skin, the hair care product of this invention can also contain one or more silicone derivatives such as dimethylpolysiloxanes, methylphenylpolysiloxanes, amino-modified silicones, alcohol-modified silicones, aliphatic-alcohol-modified silicones, polyether-modified silicones, epoxy-modified silicones, fluorine-modified silicones, cyclic silicones and alkyl-modified silicones.

Such silicone derivatives can be either simple substances or latex compositions emulsion-polymerized in accordance with the process disclosed in U.S. Pat. No. 4,228,054 which is hereby incorporated herein by reference.

Among these silicone derivatives, dimethylpolysiloxanes (polymerization degrees: 500 and higher), polyether-modified silicones, amino-modified silicones, cyclic silicones and the like are particularly preferred as they can make the hair feel good to touch.

When such a silicone derivative is added to the hair care product of this invention, its preferred proportion can be 0.01–20.0% or so, especially 0.05–10.0%.

The hair care product according to this invention can also contain, as desired, to the level of not impairing the advantageous effects of the present invention, other ingredients normally employed in hair care products, for example, additives which improve how the hair feels to the touch such as higher fatty acid salts, alkylamine oxides, fatty acid alkanol amides, squalane, lanolin, α-monoisostearylglyceryl ether, and cholesteryl sulfate; moisturizing agents such as propylene glycol, glycerin, sorbitol, amide derivatives represented, for example, by the following formula (I):

(I)

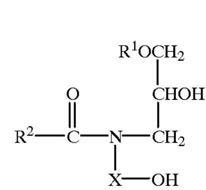

wherein $R^1$ means a $C_{10-26}$, straight- or branched-chain, saturated or unsaturated hydrocarbon group, $R^2$ denotes a $C_{9-25}$, straight- or branched-chain, saturated or unsaturated hydrocarbon group, and X stands for $-(CH_2)_m-$, m being an integer of 2–6 (see Japanese Patent Application Laid-Open No. 9913/1989), and dialkylene glycol monoalkyl ethers represented, for example, by the following formula (II);

(II)

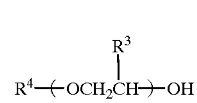

wherein $R^3$ means a hydrogen atom or methyl group, and $R^4$ denotes a $C_{1-5}$ alkyl group; viscosity regulators such as methylcellulose, carboxyvinyl polymer, hydroxyethylcellulose, polyoxyethylene glycol distearate, and ethanol; pearlizing agents; perfumes; colorants; ultraviolet absorbers; antioxidants; fungicides such as triclosan and trichlorocarban; anti-inflammatory agents such as potassium glycyrrhetinate and tocopherol acetate; anti-dandruff agents such as zinc pyrithione and octopirox; and antiseptics such as methylparaben and butylparaben.

It is preferred to regulate the pH of the hair care product of this invention to a range of about 3–10, especially 4–8 with a known acidic or alkaline reagent employed in general hair care products.

The present invention will next be described by examples. It is however to be bone in mind that the present invention is not limited by the following examples.

REFERENTIAL EXAMPLE 1

Preparation of Hair Antigens (1) Preparation of Coarse Hair Particles

Normal hair or permanent waved hair is immersed in a 11 M aqueous lithium bromide solution and then treated at 90° C. for 90 minutes over a water bath, whereby the hair is caused to swell into a rubber-like, modified state. Extra water is eliminated from the treated hair by a nylon net. The treated hair is placed in a mortar which has been cooled in advance, followed by freezing with liquefied nitrogen. While suitably supplementing liquefied nitrogen, the hair is ground by a pestle for 3 hours in the frozen state. The hair so ground is placed in a centrifugal precipitation tube and the lithium bromide washed out from the hair with deionized water. The thus-washed hair particles are collected by centrifugation. This procedure is repeated three times so that the lithium bromide is completely washed. Coarse fine particles are hence prepared. By this treatment, the hair is ground to sizes not greater than 100 μm.

(2) Preparation of Fine Hair Particles

Although the hair particles obtained above in the procedure (1) can be used as an antigen without any further treatment or processing, still finer particles are selected from the hair particles in order to provide an increased antibody titer potency. Namely, the hair particles described above are vigorously shaken in deionized water within the centrifugal precipitation tube and then allowed to stand for 1 minute. Here, fine particles remain dispersed in the supernatant although larger particles precipitate. The supernatant is then collected. A similar procedure is repeated on the remaining precipitate, whereby a supernatant containing fine particles is obtained. By centrifugation, fine particles are collected from the supernatant. When it is necessary to make the fine particles still finer, the fine particles are dispersed at 1 wt. % in distilled water and then ground several times under a pressure of 2000 psi by a French press. Fine particles are collected and prepared by lyophilization. By the above treatments, the hair is ground to sizes not greater than 10 $\mu$m.

(3) Preparation of Particulate Hair Cuticles

Particles of hair cuticles as hair constituent tissues can be prepared, for example, in the following manner. Hair is chopped to lengths not greater than 1 cm. Subsequent to removal of extra sebum with hexane, the chopped hair is sterilized with 70% ethanol. On the side, 100 ml of deionized water are placed in a Sakaguchi flask and sterilized in an autoclave. To the flask, 20 TEFLON® balls sterilized with 70% ethanol and having a diameter of about 12 mm are added together with 2 g of the sterilized hair obtained above in the procedure (2). The resulting mixture is subjected to shaking culture at 150 rpm for 2 days. The deionized water, which has been clouded with hair cuticles so separated, is recovered and lyophilized, so that particulate hair cuticles are prepared.

(4) Preparation of Particulate Hair Cortices

Particles of hair cortices (including hair medullas) are obtained by grinding hair from which hair cuticles have been removed by Vantiane. First, hair is immersed at 25° C. for 10 seconds in a 36 ppm aqueous solution of nickel chloride and then immediately rinsed with deionized water. The nickel-treated hair is then treated at 20° C. for 2 minutes with an aqueous solution of hypochlorite (which has been obtained by adjusting an approx. 5% chlorine solution with concentrated hydrochloric acid to pH 6.5), whereby hair cuticles are crushed by oxygen explosion. The resulting hair is immediately rinsed with chilled deionized water and then treated at 20° C. for 2 minutes with a 0.5% aqueous solution of sodium pyrosulfate (pH 9.5) to eliminate any remaining chlorine. Hair cuticles are then rubbed off in warm deionized water. The resulting hair is immersed for 1 minute in a 0.1 N acetic acid solution. Rinsed with chilled deionized water and finally dried, whereby decuticled hair is obtained. The decuticled hair is then ground in the same manner as the hair bundle lyophilization method described above in the procedure (1), so that particulate hair cortices are prepared.

(5) Extraction of the Keratin Protein from Hair

Hair is chopped to lengths not greater than 3 mm, added to 200 mM tris-HCl buffer (pH 9.0) containing 8 M of urea and 200 mM of 2-mercaptoethanol, and cultured at 40° C. for 2 hours under nitrogen gas. After the hair is ground in a TEFLON®-coated homogenizer, it is cultured further at 40° C. for 2 hours. The extract is centrifuged under 10,000 g for 30 minutes and the resultant supernatant is recovered. An iodoacetic acid solution is reacted to the supernatant at pH 8.0, followed by the addition of 2-mercaptoethanol to terminate the reaction. The reaction mixture is dialyzed for 2 days against deionized water and then lyophilized to provide a hair keratin protein sample. The hair keratin protein sample is dissolved again in 200 mM tris-HCl buffer (pH 9.0) containing 8 M of urea and 200 mM of 2-mercaptoethanol. The resultant mixture is dialyzed against 25 mM tris-HCl buffer (pH 7.4) in which 0.1% of sodium dodecylsulfate is contained, so that the hair-extracted keratin protein is prepared.

Test 1

Assay of Antibody Titer Potencies of Serum and Egg Yolk (1) Immunization of Hen

Particulate hair or hair constituent tissue samples obtained above in Referential Examples 1-(2) to 1-(4), respectively, were each dispersed in physiological saline and then mixed with Freund's complete adjuvant at a volume ratio of 1:1 to form a w/o emulsion. The emulsion so obtained was intramuscularly injected at 1 mg/ml to a hen four times at intervals of two weeks, whereby the hen was hyperimmunized. Blood was sampled at intervals of two weeks from the initiation of the immunization. After each blood sample was centrifuged, the resulting serum was collected. Further, eggs laid by the hen under the test were collected every week. Their yolks were separated and diluted with distilled water at a volume ratio of 1:1, whereby a twofold yolk dilution was obtained.

(2) Assay of Antibody Titer Potencies

The antibody titer potency of each of the serums and twofold yolk dilutions obtained above was determined by the following modified ELISA (enzyme-linked immunoadsorbent assay).

Namely, the particulate hair or hair constituent tissue samples obtained above in Referential Examples 1-(2) to 1-(4), respectively, were each dispersed at a concentration of 0.05% (w/v) in PBS containing 1.5% of normal rabbit serum (PBS-NRS). The resultant dispersion was poured into the individual wells of a 96-well plate ("Multiscreen-GV Filter Plate", trade name for a plate in which each well is sealed at the bottom thereof by a low-protein-adsorptive membrane filter; product of Millipore Corporation), said plate having been blocked by PBS-NRS in advance, at a rate of 50 $\mu$l per well and the solution was then sucked off.

The individual wells of each plate were then added with 50 $\mu$l aliquots of gradient-diluted solutions of the above serum or egg yolks, respectively, followed by reaction at room temperature for 1 hour. After the reaction, the plate was washed three times with PBS-T (PBS containing 0.05% of Tween-20). As a secondary antibody, biotinated anti-hen IgG antibody (product of Zymet Company; 200-fold dilution) was added at a rate of 50 $\mu$l per well, followed by reaction at room temperature for 30 minutes. After the reaction, the plate was washed three times with PBS-T. An adipin-biotin-peroxidase complex solution (product of Vector Company) was added to the wells at a rate of 50 $\mu$l per well, followed by reaction at room temperature for 30 minutes. The plate was then washed three times with PBS-T.

Next, the wells of each plate were each added with 100 $\mu$l of a peroxidase staining solution ("ABTS Kit", trade mark; product of Sumitomo Bakelite Co., Ltd.), followed by reaction at room temperature for 10 minutes. The reaction was terminated with a terminating reaction. The stained solution was recovered from each well and the absorbance ($OD_{405}$) of the well was measured. Regarding the antibody titer potencies of each serum and egg yolk samples, rates of dilution (as expressed in terms of times) of the serum and egg yolk samples, said rates of dilution giving an $OD_{405}$ value of 0.8, were determined and were then indicated in terms of their ratios to the corresponding rates of dilution of the corresponding serum and egg yolk samples of the hen before the immunization.

Using the results of the above test, changes in antibody titer potencies in the course of the immunization in the above test are shown in Table 1. As is evident from the table, it has been found that the antibodies against hair particles and hair constituent tissue particles each moves more efficiently to an egg yolk than to serum and is hence concentrated in the egg yolk.

TABLE 1

| Antigen | | Antibody titer potency 2nd week | 4th week | 6th week | 8th week | 10th week |
|---|---|---|---|---|---|---|
| Fine hair particles of Referential Example 1-(2) | Serum | 2.4 | 4.4 | 7.6 | 9.3 | 20.4 |
| | Egg yolk | 3.7 | 3.1 | 18.3 | 17.6 | 38.5 |
| Particulate hair cuticles of Referential Example 1-(3) | Serum | 1.0 | 2.9 | 3.6 | 2.5 | 7.8 |
| | Egg yolk | 1.5 | 3.6 | 7.4 | 8.2 | 13.6 |
| Particulate hair cortices of Referential Example 1-(4) | Serum | 2.2 | 8.5 | — | 8.2 | 20.9 |
| | Egg yolk | 2.4 | 3.4 | 33.6 | 23.1 | 46.9 |

REFERENTIAL EXAMPLE 2

Preparation Method of Hen's Egg Antibody (1) Preparation of Antibody-containing Yolk Protein Each of the particulate hair samples and particulate hair constituent tissue samples obtained above in Referential Examples 1-(1) to 1-(5), respectively, was dispersed in physiological saline. The resulting dispersion was mixed with Freund's complete adjuvant, and a hen was then hyperimmunized with the mixture (four intramuscular injections at 1 mg/ml each). An antibody was purified from an egg laid by the hen. Described specifically, the egg yolk and a 1.5 mg/ml aqueous solution of λ-carrageenan were mixed at a volume ratio of 1:5, and the resulting coagulate of lipoproteins was removed by centrifugal separation to purify the supernatant. The supernatant so obtained contained a yolk-derived antibody at a recovery rate of about 80%.

(2) Preparation of Purified, Yolk-derived Anti-hair Antibody

From the supernatant prepared above in Procedure (1), crystals of the yolk-derived antibody were obtained by the fractionating salting-out method which makes use of sodium sulfate. The yolk-derived antibody was obtained as a 17% (w/v) sodium sulfate salt precipitate, and other impurities were removed as a centrifugal supernatant.

EXAMPLE 1

Hair Treatment Formulations

Hair treatment formulations of the compositions shown below in Table 2 were prepared and their performance evaluation tests were conducted. The results of the tests are also shown in Table 2.

Evaluation Method (1) Twenty grams of the hair (about 15–20 cm long) of a Japanese female, said hair having been subjected to cold permanent waving three times until that time, were bundled and washed with an ordinary shampoo. The hair was uniformly coated with 2 g of each hair treatment formulation. After the hair was rinsed for 30 minutes by running water, it was towel-dried and then blow-dried. With respect to the hair so dried, its flexibility, oiliness, moisturized feeling and smoothness were evaluated in accordance with the following standards.

Flexibility:

A: Very flexible
B: Flexible
C: Not stiff but not flexible
D: Stiff

Oiliness:

A: Very little
B: Little
C: Not little but not oily
D: Very oily

Luster:

A: Very much
B: Much
C: Not much but not free of luster
D: No luster

Smoothness:

A: Very much
B: Much
C: Not much but not completely unsmooth
D: Not smooth (2) Using hair bundles treated as in the above evaluation (1), the degrees of occurrence of split hair after brushed a predetermined number of times were compared with those before the brushing and evaluated in accordance with the following standards.

A: No increase in split hair is recognized.
B: No substantial increase in split hair is recognized.
C: A small increase in split hair is recognized.
D: A substantial increase in split hair is recognized.

TABLE 2

| Ingredient | Invention product 1 | 2 | 3 | 4 | 5 |
|---|---|---|---|---|---|
| Stearyltrimethylammonium chloride | 1 | 1 | 1 | 1 | 1 |
| N-(2-Decyl)tetradecyl-N,N,N-trimethylaminonium chloride | 1 | 1 | 1 | 1 | 1 |
| Cetyl alcohol | 2 | 2 | 2 | 2 | 2 |
| Propylene glycol | 4 | 4 | 4 | 4 | 4 |
| Diethylene glycol monoethyl ether | 4 | 4 | 4 | 4 | 4 |
| Yblk protein of Referential Example 2-(1) [antigen: the coarse hair particles of Referential Example 1-(1)] | 0.01 | 0.1 | 1.0 | 10 | — |
| Purified antibody of Referential Example 2-(2) [antigen: coarse hair particles of Referential Example 1-(1)] | — | — | — | — | 1.0 |
| Purified water | Balance | Balance | Balance | Balance | Balance |
| Evaluated Flexibility | B | B | A | A | A |

TABLE 2-continued

| Ingredient | | Invention product | | | | |
|---|---|---|---|---|---|---|
| | | 1 | 2 | 3 | 4 | 5 |
| property | Oiliness | A | A | A | A | A |
| | Luster | B | B | A | A | A |
| | Smoothness | B | B | A | A | A |
| | Degree of occurrence of split hair | B | A | A | A | A |

EXAMPLE 2

Shampoo Formulations

Shampoo formulations of the compositions shown in Table 3 were prepared and their performance evaluation tests were conducted. The results of the tests are also shown in Table 3.

Evaluation Method (1) About 20 g of the hair (about 15–20 cm) of a Japanese female, said hair having been subjected to cold permanent waving three times until that time, were bundled. After the hair was soaked with warm water of about 40° C., the hair was thoroughly coated with 1 g of each shampoo formulation. The shampoo formulation was lathered for 1 minute to shampoo the hair. The hair was rinsed with running water and then dried. With respect to the dried hair, its flexibility, oiliness, moisturized feeling and smoothness were evaluated. The evaluation standards in Example 1-(1) were followed exactly.

(2) Using hair bundles treated as in the above evaluation (1), the degrees of occurrence of split hair after brushed a predetermined number of times were evaluated in comparison with those before the brushing. The evaluation standards in Example 1-(2) were followed exactly.

TABLE 3

| Ingredient | | Invention product | | | | Comp. product | |
|---|---|---|---|---|---|---|---|
| | | 6 | 7 | 8 | 9 | 3 | 4 |
| Polyoxyethylene (2.5) sodium lauryl sulfate | | 20 | — | — | — | 20 | — |
| Polyoxyethylene (2.5) lauryl sulfate triethanolamine | | — | 20 | — | — | — | 20 |
| Lauryl sulfate triethanolamine | | — | — | 20 | — | — | — |
| Sodium alpha-olefinsulfonate | | — | — | — | — | — | — |
| N-Lauroly-N'-carboxysethyl-N'-(2-hydroxyethyl)ethylenediamine TEA salt | | — | — | — | 20 | — | — |
| Coconut oil fatty acid diethanolamide | | 3 | 3 | 3 | 3 | 3 | 3 |
| Yolk protein of Referential Example 2-(1) [antigen: the coarse hair particles of Referential Example 1-(2)] | | 1 | — | — | — | — | — |
| Yolk protein of Referential Example 2-(1) [antigen: the particulate hair cuticles of Referential Example 1-(3)] | | — | 1 | — | — | — | — |
| Yolk protein of Referential Example 2-(1) [antigen: the particulate hair cortices of Referential Example 1-(4)] | | — | — | 1 | — | — | — |
| Yolk protein of Referential Example 2-(1) [antigen: the extracted keratin protein of Referential Example 1-(5)] | | | | | | | |
| Purified water | | Balance | Balance | Balance | Balance | Balance | Balance |
| Evaluated | Flexibility | B | B | B | B | D | D |
| property | Oiliness | A | A | A | A | D | D |
| | Luster | B | B | B | B | D | D |
| | Smoothness | A | A | A | A | D | D |
| | Degree of occurrence of split hair | A | A | A | A | D | D |

EXAMPLE 3

Hair Treatment Formulations

Hair treatment formulations were prepared as in Example 1 except that, instead of the yolk-derived anti-hair antibody obtained in Referential Example 2-(1) [antigen: the coarse hair particles obtained in Referential Example 1-(1)], yolk-derived anti-hair antibodies purified in accordance with the method of Referential Example 2-(2) [antigens: (i) the fine hair particles obtained in Referential Example 1-(2), (ii) the particulate hair cuticles obtained in Referential Example 1-(3), (iii) the particulate hair cortices obtained in Referential Example 1-(4), and (iv) the extracted keratin protein obtained in Referential Example 1-(5)] were used. Those hair treatment formulations were all excellent in softness, luster, smoothness and the like.

We claim:

1. A hair care product comprising a yolk antibody which has been obtained from an egg of a domestic fowl immunized using human hair as an antigen.

2. The hair care product of claim 1, wherein the domestic fowl is a egg-breed domestic fowl selected from the group consisting of hen, duck and quail.

3. The hair care product of claim 1, wherein the human hair is selected from the group consisting of particulate normal human hair, particulate human hair damaged by permanent waving, particulate human hair cuticles, particulate human hair cortices, the keratin protein extracted from the human hair, and hydrolysates of the keratin protein.

4. The hair care product of claim 1, wherein the yolk antibody is contained in a proportion of 0.001–5% based on the hair care product when calculated as a fully-purified lyophilization product.

5. The hair care product of claim 1, wherein said yolk antibody is a lyophilization product of a supernatant obtained by adding an aqueous solution of λ-carrageenan to the yolk of said egg, said yolk antibody being present in a proportion of 0.01–50 wt. % of said hair care product.

6. The hair care product of claim 5, wherein said yolk antibody is present in a proportion of 0.01–20 wt. % of said hair care product.

7. The hair care product of claim 4, wherein said yolk antibody is present in a proportion of 0.005–1 wt. % of said hair care product.

8. The hair care product of claim 1, further comprising an anionic surfactant, an amphoteric surfactant, a nonionic surfactant, a cationic surfactant, or a combination thereof, and the balance of said hair care product comprising purified water.

9. The hair care product of claim 8, further comprising 0.01–40.0 wt. % of an anionic surfactant, an amphoteric surfactant, a nonionic surfactant, a cationic surfactant, or a combination thereof, and the balance of said hair care product comprising purified water.

10. The hair care product of claim 8, further comprising a cationic polymer.

11. The hair care product of claim 9, further comprising 0.05–20.0% of a cationic polymer.

12. The hair care product of claim 10, further comprising a silicone.

13. The hair care product of claim 11, further comprising 0.01–20.0 wt. % of a silicone.

14. The hair care product of claim 12, wherein said silicone is selected from the group consisting of dimethylpolysiloxanes, methylphenylpolysiloxanes, amino-modified silicones, alcohol-modified silicones, polyether-modified silicones, epoxy-modified silicones, fluorine-modified silicones, cyclic silicones and alkyl-modified silicones.

15. The hair care product of claim 13, wherein said silicone is selected from the group consisting of dimethylpolysiloxanes, methylphenylpolysiloxanes, amino-modified silicones, alcohol-modified silicones, polyether-modified silicones, epoxy-modified silicones, fluorine-modified silicones, cyclic silicones and alkyl-modified silicones.

16. The hair care product of claim 14, wherein said silicone is an aliphatic-alcohol-modified silicone.

17. The hair care product of claim 15, wherein said silicone is an aliphatic-alcohol-modified silicone.

* * * * *